(12) United States Patent
Steinhauer et al.

(10) Patent No.: US 11,626,199 B2
(45) Date of Patent: *Apr. 11, 2023

(54) VENTILATION MANAGEMENT SYSTEM

(71) Applicant: Vyaire Medical Capital LLC, Mettawa, IL (US)

(72) Inventors: Tom Steinhauer, San Diego, CA (US); Willis Lam, San Diego, CA (US); Mark Rogers, Irvine, CA (US); Terry Blansfield, Orange, CA (US); Stephen J. Birch, Mission Viejo, CA (US)

(73) Assignee: VYAIRE MEDICAL CAPITAL LLC, Mettawa, IL (US)

( * ) Notice: Subject to any disclaimer, the term of this patent is extended or adjusted under 35 U.S.C. 154(b) by 35 days.

This patent is subject to a terminal disclaimer.

(21) Appl. No.: 16/857,060

(22) Filed: Apr. 23, 2020

(65) Prior Publication Data

US 2020/0246568 A1 Aug. 6, 2020

Related U.S. Application Data

(63) Continuation of application No. 15/394,346, filed on Dec. 29, 2016, now Pat. No. 10,646,674, which is a
(Continued)

(51) Int. Cl.
*G16H 20/40* (2018.01)
*A61M 16/00* (2006.01)
(Continued)

(52) U.S. Cl.
CPC ........ *G16H 20/40* (2018.01); *A61M 16/0051* (2013.01); *A61M 16/0057* (2013.01);
(Continued)

(58) Field of Classification Search
CPC .............. A61M 16/0057; A61M 16/00; A61M 2205/6009; A61M 2205/3584;
(Continued)

(56) References Cited

U.S. PATENT DOCUMENTS

| 4,988,336 A | 1/1991 | Kohn |
| 5,065,315 A | 11/1991 | Garcia |

(Continued)

FOREIGN PATENT DOCUMENTS

| CN | 109661197 A | 4/2019 |
| EP | 2181726 A1 | 5/2010 |

(Continued)

OTHER PUBLICATIONS

Fairley, H. Barrie, and B.A. Britt. "The adequacy of the air-mix control in ventilators operated from an oxygen source." Canadian Medical Association Journal 90.25 (1964): 1394.

(Continued)

*Primary Examiner* — Colin W Stuart
*Assistant Examiner* — Douglas Y Sul
(74) *Attorney, Agent, or Firm* — Morgan, Lewis & Bockius LLP

(57) ABSTRACT

A ventilation management system stores an initial configuration profile including a set of operating parameters for operating one or more respective ventilation devices. The system receives first ventilator data from a first ventilation device at a first location, and second ventilator data from a second ventilation device at a second location, the first and second ventilation devices being configured to operate based on the initial configuration profile, wherein the received first ventilator data comprises one or more current operating parameters of the first ventilation device, or physiological data obtained from a patient associated with the first ventilation device. The system modifies the initial configuration profile for use by the first ventilation device based on the received first ventilation data and provides the modified configuration profile to the first ventilation device. The modified configuration profile is implemented by the first
(Continued)

ventilation device when approved by a clinician or the patient.

20 Claims, 8 Drawing Sheets

Related U.S. Application Data continuation of application No. 13/830,730, filed on Mar. 14, 2013, now Pat. No. 9,821,129, which is a continuation-in-part of application No. 13/287,419, filed on Nov. 2, 2011, now abandoned.

(51) Int. Cl.
- *G16H 10/60* (2018.01)
- *G16H 40/63* (2018.01)
- *G16H 40/67* (2018.01)
- *A61M 16/10* (2006.01)

(52) U.S. Cl.
CPC ........ *A61M 16/021* (2017.08); *A61M 16/026* (2017.08); *A61M 16/1005* (2014.02); *G16H 10/60* (2018.01); *G16H 40/63* (2018.01); *G16H 40/67* (2018.01); *A61M 2205/3553* (2013.01); *A61M 2205/3561* (2013.01); *A61M 2205/3584* (2013.01); *A61M 2205/3592* (2013.01); *A61M 2205/502* (2013.01); *A61M 2205/505* (2013.01); *A61M 2205/52* (2013.01); *A61M 2205/6009* (2013.01); *A61M 2205/609* (2013.01); *A61M 2205/6018* (2013.01); *A61M 2205/6054* (2013.01); *A61M 2205/6072* (2013.01); *A61M 2230/005* (2013.01); *A61M 2230/202* (2013.01); *A61M 2230/42* (2013.01); *A61M 2230/432* (2013.01); *A61M 2230/435* (2013.01); *A61M 2230/46* (2013.01)

(58) Field of Classification Search
CPC ...... A61M 2205/505; A61M 2205/609; A61M 2205/3553; A61M 2205/6087; A61M 2205/6072; A61M 2205/6018; A61M 2230/435; A61M 2230/432; A61M 2230/202

See application file for complete search history.

(56) References Cited

U.S. PATENT DOCUMENTS

| | | | |
|---|---|---|---|
| 5,544,649 A | 8/1996 | David et al. | |
| 5,626,151 A | 5/1997 | Linden | |
| 5,881,723 A | 3/1999 | Wallace et al. | |
| 5,931,160 A | 8/1999 | Gilmore et al. | |
| 5,987,519 A | 11/1999 | Peifer et al. | |
| 6,148,814 A | 11/2000 | Clemmer et al. | |
| 6,158,430 A | 12/2000 | Pfeiffer et al. | |
| 6,158,433 A | 12/2000 | Ong et al. | |
| 6,349,724 B1 | 2/2002 | Burton et al. | |
| 6,369,847 B1 | 4/2002 | James et al. | |
| 6,406,426 B1 | 6/2002 | Reuss et al. | |
| 6,459,933 B1 | 10/2002 | Lurie et al. | |
| 6,551,243 B2* | 4/2003 | Bocionek | G16H 10/60 |
| | | | 600/300 |
| 6,666,820 B1 | 12/2003 | Poole | |
| 6,839,753 B2 | 1/2005 | Biondi et al. | |
| 6,955,170 B1 | 10/2005 | Mullins et al. | |
| 7,225,809 B1 | 6/2007 | Bowen et al. | |
| 7,237,205 B2 | 6/2007 | Sarel | |
| 7,334,578 B2 | 2/2008 | Biondi et al. | |
| 7,395,216 B2* | 7/2008 | Rosenfeld | A61B 5/412 |
| | | | 705/2 |
| 7,610,099 B2 | 10/2009 | Almendinger et al. | |
| 7,668,596 B2 | 2/2010 | Von Arx et al. | |
| 7,677,246 B2 | 3/2010 | Kepler et al. | |
| 7,698,156 B2 | 4/2010 | Martucci et al. | |
| 7,933,780 B2 | 4/2011 | De La Huerga | |
| 8,015,972 B2* | 9/2011 | Pirzada | A61B 5/746 |
| | | | 128/204.21 |
| 8,255,238 B2 | 8/2012 | Powell et al. | |
| 8,321,284 B2 | 11/2012 | Clements et al. | |
| 8,327,846 B2 | 12/2012 | Bowditch et al. | |
| 8,447,629 B2 | 5/2013 | Rappaport et al. | |
| 8,522,779 B2 | 9/2013 | Lee et al. | |
| 8,695,593 B2 | 4/2014 | Tehrani | |
| 9,058,741 B2 | 6/2015 | Steinhauer et al. | |
| 9,072,849 B2 | 7/2015 | Steinhauer et al. | |
| 9,177,109 B2 | 11/2015 | Steinhauer et al. | |
| 9,327,090 B2 | 5/2016 | Steinhauer et al. | |
| 9,352,110 B2 | 5/2016 | Steinhauer et al. | |
| 9,687,618 B2 | 6/2017 | Steinhauer et al. | |
| 9,737,676 B2 | 8/2017 | Steinhauer et al. | |
| 9,821,129 B2* | 11/2017 | Steinhauer | G16H 10/60 |
| 10,646,674 B2* | 5/2020 | Steinhauer | A61M 16/021 |
| 2001/0016821 A1 | 8/2001 | DeBusk et al. | |
| 2001/0027791 A1 | 10/2001 | Wallace et al. | |
| 2002/0022973 A1 | 2/2002 | Sun et al. | |
| 2002/0026941 A1 | 3/2002 | Biondi et al. | |
| 2002/0077862 A1 | 6/2002 | Auer et al. | |
| 2002/0091309 A1 | 7/2002 | Auer | |
| 2002/0120676 A1 | 8/2002 | Biondi et al. | |
| 2002/0133061 A1 | 9/2002 | Manetta | |
| 2003/0050802 A1 | 3/2003 | Jay et al. | |
| 2003/0101076 A1 | 5/2003 | Zaleski | |
| 2004/0077934 A1 | 4/2004 | Massad | |
| 2004/0249675 A1 | 12/2004 | Stark et al. | |
| 2005/0108057 A1 | 5/2005 | Cohen et al. | |
| 2005/0137653 A1 | 6/2005 | Friedman et al. | |
| 2005/0143632 A1 | 6/2005 | Elaz et al. | |
| 2005/0151640 A1 | 7/2005 | Hastings | |
| 2005/0188083 A1 | 8/2005 | Biondi et al. | |
| 2005/0192845 A1 | 9/2005 | Brinsfield et al. | |
| 2005/0267348 A1 | 12/2005 | Wollenweber et al. | |
| 2005/0268916 A1 | 12/2005 | Mumford et al. | |
| 2006/0031095 A1 | 2/2006 | Barth et al. | |
| 2006/0144401 A1 | 7/2006 | Boelt | |
| 2006/0162727 A1 | 7/2006 | Biondi et al. | |
| 2006/0174883 A1 | 8/2006 | Alysworth et al. | |
| 2006/0180150 A1 | 8/2006 | Dittmann | |
| 2006/0189854 A1* | 8/2006 | Webb | A61B 5/24 |
| | | | 600/300 |
| 2006/0206011 A1 | 9/2006 | Higgins et al. | |
| 2006/0289020 A1 | 12/2006 | Tabak et al. | |
| 2007/0005621 A1 | 1/2007 | Lesh et al. | |
| 2007/0015976 A1 | 1/2007 | Miesel et al. | |
| 2007/0023045 A1 | 2/2007 | Kwok et al. | |
| 2007/0033072 A1 | 2/2007 | Bildirici | |
| 2007/0276696 A1 | 11/2007 | Gauvin et al. | |
| 2007/0283958 A1 | 12/2007 | Naghavi | |
| 2008/0053438 A1 | 3/2008 | DeVries et al. | |
| 2008/0072902 A1 | 3/2008 | Setzer et al. | |
| 2008/0077436 A1 | 3/2008 | Muradia | |
| 2008/0086691 A1 | 4/2008 | Hopermann et al. | |
| 2008/0091466 A1 | 4/2008 | Butler et al. | |
| 2008/0097793 A1 | 4/2008 | Dicks et al. | |
| 2008/0097913 A1 | 4/2008 | Dicks et al. | |
| 2008/0140160 A1 | 6/2008 | Goetz et al. | |
| 2008/0230064 A1 | 9/2008 | Tham | |
| 2008/0271736 A1 | 11/2008 | Leonard et al. | |
| 2008/0288023 A1 | 11/2008 | John | |
| 2008/0308101 A1 | 12/2008 | Spandorfer | |
| 2008/0312548 A1 | 12/2008 | Hartley wet al. | |
| 2009/0044803 A1 | 2/2009 | Fernandez | |
| 2009/0054735 A1 | 2/2009 | Higgins et al. | |
| 2009/0112160 A1 | 4/2009 | Yang | |
| 2009/0171696 A1 | 7/2009 | Allard et al. | |
| 2009/0184823 A1 | 7/2009 | Tessier | |
| 2009/0229610 A1 | 9/2009 | Oates et al. | |
| 2009/0241956 A1* | 10/2009 | Baker, Jr. | A61M 16/12 |
| | | | 128/204.23 |
| 2009/0293886 A1 | 12/2009 | Dedrick et al. | |
| 2009/0326389 A1 | 12/2009 | Ralfs | |

(56) References Cited

U.S. PATENT DOCUMENTS

| | | |
|---|---|---|
| 2010/0071697 A1 | 3/2010 | Jafari et al. |
| 2010/0078017 A1 | 4/2010 | Andrieux et al. |
| 2010/0083968 A1 | 4/2010 | Wondka et al. |
| 2010/0085156 A1 | 4/2010 | Tucker |
| 2010/0108064 A1 | 5/2010 | Blackwell et al. |
| 2010/0161345 A1 | 6/2010 | Cain et al. |
| 2010/0202354 A1 | 8/2010 | Ho |
| 2010/0287006 A1* | 11/2010 | Cannon ............... G16H 40/20 705/3 |
| 2010/0288279 A1 | 11/2010 | Seiver et al. |
| 2010/0298718 A1 | 11/2010 | Gilham et al. |
| 2010/0318155 A1 | 12/2010 | Mahajan et al. |
| 2010/0326446 A1 | 12/2010 | Behlmaier |
| 2011/0011400 A1 | 1/2011 | Gentner et al. |
| 2011/0034783 A1 | 2/2011 | Lisogurski et al. |
| 2011/0073107 A1 | 3/2011 | Rodman et al. |
| 2011/0078253 A1 | 3/2011 | Chan et al. |
| 2011/0087756 A1 | 4/2011 | Biondi et al. |
| 2011/0107251 A1 | 5/2011 | Guaitoli et al. |
| 2011/0108034 A1 | 5/2011 | Viertio-Oja |
| 2011/0112442 A1 | 5/2011 | Meger et al. |
| 2011/0120470 A1* | 5/2011 | Bowerbank ............ G16H 20/40 128/204.23 |
| 2011/0139155 A1 | 6/2011 | Farrell et al. |
| 2011/0178373 A1 | 7/2011 | Pacey et al. |
| 2011/0208539 A1 | 8/2011 | Lynn |
| 2011/0231505 A1 | 9/2011 | Chan et al. |
| 2011/0238441 A1 | 9/2011 | Callas |
| 2011/0319322 A1 | 12/2011 | Bashan et al. |
| 2012/0082036 A1 | 4/2012 | Abedi et al. |
| 2012/0108984 A1 | 5/2012 | Bennett et al. |
| 2012/0109240 A1 | 5/2012 | Zhou et al. |
| 2012/0118285 A1 | 5/2012 | Wondka et al. |
| 2012/0137250 A1 | 5/2012 | Milne et al. |
| 2012/0145153 A1 | 6/2012 | Bassin et al. |
| 2012/0216809 A1 | 8/2012 | Milne et al. |
| 2012/0272955 A1 | 11/2012 | Cool et al. |
| 2012/0330177 A1 | 12/2012 | Al-Rawas et al. |
| 2013/0032147 A1 | 2/2013 | Robinson et al. |
| 2013/0054264 A1* | 2/2013 | Baronov ............ A61M 16/0003 705/2 |
| 2013/0104889 A1 | 5/2013 | Steinhauer et al. |
| 2013/0104890 A1 | 5/2013 | Steinhauer et al. |
| 2013/0104891 A1 | 5/2013 | Steinhauer et al. |
| 2013/0104892 A1 | 5/2013 | Steinhauer et al. |
| 2013/0104893 A1 | 5/2013 | Steinhauer et al. |
| 2013/0104894 A1 | 5/2013 | Steinhauer et al. |
| 2013/0104895 A1 | 5/2013 | Steinhauer et al. |
| 2013/0104897 A1 | 5/2013 | Steinhauer et al. |
| 2013/0106864 A1 | 5/2013 | Boyer et al. |
| 2013/0110528 A1 | 5/2013 | Steinhauer et al. |
| 2013/0110529 A1 | 5/2013 | Steinhauer et al. |
| 2013/0110530 A1 | 5/2013 | Steinhauer et al. |
| 2013/0110546 A1 | 5/2013 | Steinhauer et al. |
| 2013/0110924 A1 | 5/2013 | Steinhauer et al. |
| 2013/0186405 A1 | 7/2013 | Krzyzanowski et al. |
| 2013/0199533 A1 | 8/2013 | Steinhauer et al. |
| 2014/0000604 A1 | 1/2014 | Steinhauer et al. |
| 2014/0000605 A1 | 1/2014 | Steinhauer et al. |
| 2014/0000607 A1 | 1/2014 | Steinhauer et al. |
| 2014/0000608 A1 | 1/2014 | Steinhauer et al. |
| 2014/0002246 A1 | 1/2014 | Steinhauer et al. |
| 2014/0006041 A1 | 1/2014 | Steinhauer et al. |
| 2014/0006052 A1 | 1/2014 | Steinhauer et al. |
| 2014/0158124 A1 | 6/2014 | L'her et al. |
| 2015/0182712 A1 | 7/2015 | Kelly et al. |
| 2019/0184119 A1 | 6/2019 | Crawford et al. |

FOREIGN PATENT DOCUMENTS

| | | |
|---|---|---|
| EP | 2773410 A1 | 9/2014 |
| EP | 3503795 A1 | 7/2019 |
| JP | 2019528153 A | 10/2019 |
| WO | 2002/044993 | 6/2002 |
| WO | 2011/087111 | 7/2011 |
| WO | WO-2013067223 A1 | 5/2013 |
| WO | WO-2018038853 A1 | 3/2018 |

OTHER PUBLICATIONS

Krieger, Bruce P., et al. "Initial experience with a central respiratory monitoring unit as a cost-saving alternative to the intensive care unit for Medicare patients who require long-term ventilator support." CHEST Journal 93.2 (1988): 395-397.

Simonds, A. K. "Streamlining wearning: protocols and weaning units." Thorax 60.3 (2005): 175-182.

Chipman, Daniel W., et al. "Performance comparison of 15 transport ventilators." Respiratory care 52.6 (2007): 740-751.

Shimpi, A.L., "iphone 3GS Performance: A Significant Performance Bump," Anand Tech (2009), http://www.anandtech.com/show/2790.

Govoni, et al., "An Improved Telemedicine System for Remote Titration and Optimization of Home Mechanical Ventilation", Biomedical Engineering Conference (CIBEC), 2010 5th Cairo International, IEEE, Dec. 16, 2010, pp. 66-69, XP031979754.

"Medicare Quarterly Provider Compliance Newsletter", Oct. 2011, 21 pages, vol. 2, Issue 1, CMS.

Title: CPAP Equipment: CPAP Software Date Archived: May 12, 2012 Publisher: cpap.com.

International Search Report and Written Opinion for International Application No. PCT/US2012/063119, dated Mar. 29, 2013, 8 pages.

"Solutions," retrieved on Sep. 16, 2013, 1 page, Theronyx, retrieved from <http://www.theronyx.com/solutions>.

"Vital Sync Virtual Patient monitoring Platform 2.0," retrieved on Sep. 16, 2013, 2 pages, Covidien, retrieved from <http://www.covidien.com/RMS/pages.aspx?page+Product/Vital-Sync-Vitrual-Patient-Monitoring-Platform>.

International Search Report for International Application No. PCT/US2013/057860, dated Nov. 7, 2013, 2 pages.

International Search Report for International Application No. PCT/US2013/057862, dated Dec. 12, 2013, 2 pages.

International Preliminary Report on Patentability for International Application No. PCT/US2012/063119, dated Feb. 27, 2014, 14 pages.

Extended European Search Report for Application No. 12844716.6, dated Jan. 4, 2016, 12 pages.

Extended European Search Report for Application No. 13878057.2, dated Oct. 4, 2016, 8 pages.

Canadian Office Action for Application No. 2904004, dated Jul. 3, 2019, 5 pages.

European Office Action for Application No. 12844716.6, dated Nov. 6, 2017, 7 pages.

Canadian Office Action for Application No. 2904004, dated Aug. 10, 2020, 4 pages.

Extended European Search Report for Application No. 20151238.1, dated May 15, 2020, 7 pages.

Extended European Search Report for Application No. 21187978.9, dated Nov. 24, 2021, 11 pages.

European Office Action for Application No. 20151238.1, dated Mar. 21, 2022, 4 pages.

* cited by examiner

VENTILATION MANAGEMENT SYSTEM

CROSS-REFERENCE TO RELATED APPLICATIONS

The present application is a continuation application of U.S. patent application Ser. No. 15/394,346, entitled "VENTILATION MANAGEMENT SYSTEM," filed on Dec. 29, 2016, now U.S. Pat. No. 10,646,674, which is a continuation application of U.S. patent application Ser. No. 13/830,730, entitled "VENTILATION MANAGEMENT SYSTEM," filed on Mar. 14, 2013, now U.S. Pat. No. 9,821,129, which is a continuation-in-part application of U.S. patent application Ser. No. 13/287,419, entitled "BI-DIRECTIONAL VENTILATOR COMMUNICATION," filed on Nov. 2, 2011. The disclosures of these applications is hereby incorporated by reference in their entirety for all purposes.

BACKGROUND

Field

The present disclosure generally relates to medical devices, and more particularly to the configuration of a ventilator.

Description of the Related Art

Medical ventilation systems (or "ventilators," colloquially called "respirators") are machines that are typically used to mechanically provide breathable air or blended gas to lungs in order to assist a patient in breathing. Ventilation systems are chiefly used in intensive care medicine, home care, emergency medicine, and anesthesia. Common ventilation systems are limited to a single direction of communication, and as such are configured to provide information related to the ventilation system for display, but not receive information from a remote source for any purpose to control the ventilator. For example, common ventilation systems send outbound data to another entity, such as a display device, in order to display ventilator settings.

SUMMARY

According to certain embodiments of the present disclosure, a ventilation system is provided. The system includes a ventilation device that is configured to provide breathable air to a patient according to certain operating parameters, a memory that includes instructions, and a processor. The processor is configured to execute the instructions to receive, over a network, at least one of patient data, order data, configuration data, user data, or rules or protocols, and provide a modification of operating parameters of the ventilation device based on the received patient data, order data, configuration data, user data, or rules or protocols.

According to certain embodiments of the present disclosure, a method for configuring a ventilator is provided. The method includes receiving, over a network, at least one of patient data, order data, configuration data, user data, or rules or protocols, and providing a modification of operating parameters of a ventilation device that is configured to provide breathable air to a patient according to the operating parameters based on the received patient data, order data, configuration data, user data, or rules or protocols.

According to certain embodiments of the present disclosure, a machine-readable storage medium includes machine-readable instructions for causing a processor to execute a method for configuring a ventilator is provided. The method includes receiving, over a network, at least one of patient data, order data, configuration data, user data, or rules or protocols, and providing a modification of operating parameters of a ventilation device that is configured to provide breathable air to a patient according to the operating parameters based on the received patient data, order data, configuration data, user data, or rules or protocols.

According to certain embodiments of the present disclosure, a ventilator management system is provided. The system includes a memory that includes an initial configuration profile configured to designate operating parameters for a ventilation device, and a processor. The processor is configured to receive ventilator data from the ventilation device, the ventilator data includes at least one of operating parameters of the ventilation device or physiological statistics of a patient associated with the ventilation device, and determine, based on the ventilator data, a modification to the initial configuration profile for the ventilation device. The processor is also configured to generate a modified configuration profile for the ventilation device based on the determined modification.

According to certain embodiments of the present disclosure, a method for managing a plurality of ventilators is provided. The method includes receiving ventilator data from the ventilation device, the ventilator data includes at least one of operating parameters of the ventilation device or physiological statistics of a patient associated with the ventilation device, and determining, based on the ventilator data, a modification to an initial configuration profile for the ventilation device. The method also includes generating a modified configuration profile for the ventilation device based on the determined modification.

According to certain embodiments of the present disclosure, a machine-readable storage medium includes machine-readable instructions for causing a processor to execute a method for managing a plurality of ventilators is provided. The method includes receiving ventilator data from the ventilation device, the ventilator data includes at least one of operating parameters of the ventilation device or physiological statistics of a patient associated with the ventilation device, and determining, based on the ventilator data, a modification to an initial configuration profile for the ventilation device. The method also includes generating a modified configuration profile for the ventilation device based on the determined modification.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

In the following detailed description, numerous specific details are set forth to provide a full understanding of the present disclosure. It will be apparent, however, to one ordinarily skilled in the art that the embodiments of the present disclosure may be practiced without some of these specific details. In other instances, well-known structures and techniques have not been shown in detail so as not to obscure the disclosure.

Certain aspects of the disclosed system provide ventilation systems with two-way communication. Specifically, in addition to permitting a ventilation system to output basic ventilation data such as physiological statistics, the disclosed ventilation systems permit output of additional information such as ventilator settings, notifications, patient information, ventilation waveforms, loops or trended data ("scalars"), and ventilation monitoring information. The disclosed ventilation systems also permit input of configuration profiles, rules and clinical protocols, user data, notifications, preprogramming, patient data, and lab results. The disclosed ventilation systems are configured to operate according to the received configuration profiles, rules, and protocols, and in view of the user data, notifications, preprogramming, patient data, and lab results. The data for the ventilation system can also be "contextualized" (e.g., associated with a patient and/or caregiver) using various wired and wireless techniques. The disclosed ventilation systems are configured to provide the output of additional information to, for example, a ventilation management system.

The disclosed ventilation management system is configured to receive the information from one or many ventilation systems, analyze the information, and determine new or modified configuration profiles, rules, and clinical protocols from the received information. The information may be received wired or wirelessly over a network. The disclosed ventilation management system is also configured to provide the new or modified configuration profiles, rules, and clinical protocols back to one or many of the ventilation systems. The ventilation systems managed by the ventilation management system can be located either in a healthcare institution (e.g., a hospital) or outside of a healthcare institution (e.g., a home or other care site). Both the ventilation systems and the ventilation management systems are configured to cache data, for example, when the network is not available, so that data may be saved for later transmission.

Figure 1:
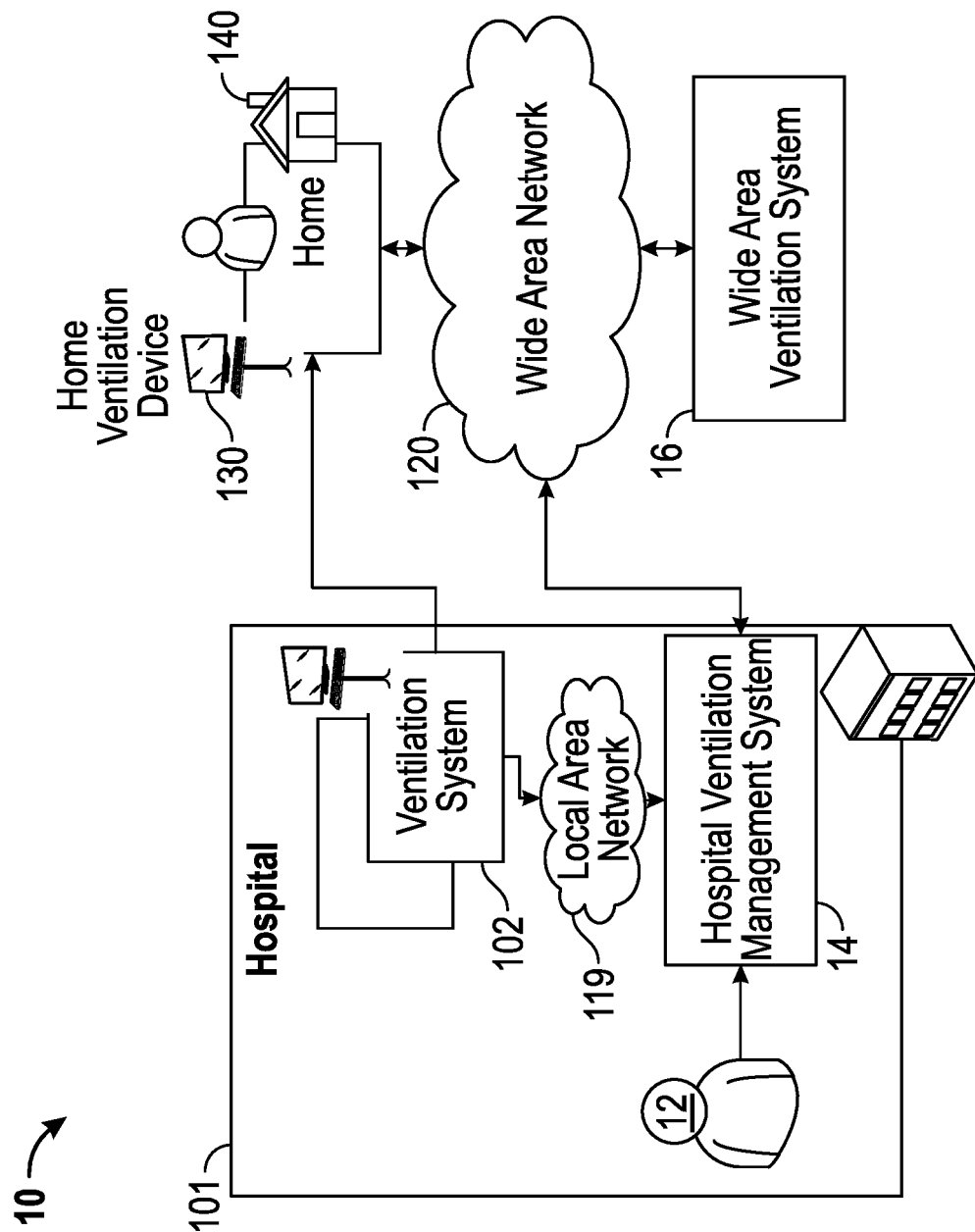
FIG. 1 illustrates an example architecture for a ventilator management system.

FIG. 1 illustrates an example architecture 10 for a ventilator management system. The architecture 10 includes a ventilation system 102 and a hospital ventilation management system 14 connected over a local area network (LAN) 119 in a hospital 101, and a home ventilation device 130 in a home 140 connected to a wide area ventilation management system 16 over a wide area network (WAN) 120. The hospital ventilation management system 14, which can be configured, for example, by a clinician 12, other healthcare provider, or administrator, is connected to the wide area ventilation management system 16 through the WAN 120. Furthermore, the home ventilation device 130 may operate substantially similar to, and be configured substantially the same as, the ventilation system 102 of the hospital 101, except that the home ventilation device 130 operates in the home 140.

Each of the ventilation systems 102 is configured to mechanically move breathable air into and out of lungs in order to assist a patient in breathing. The ventilation systems 102 can provide ventilator data, such as notifications, settings, monitor information (e.g., physiological statistics), and scalars to the hospital ventilation management system 14. The ventilation system 102 includes a device having appropriate processor, memory, and communications capabilities for processing and providing ventilator data to the hospital ventilation management system 14. Similarly, the hospital ventilation management system 14 is configured to provide user data, notifications, pre-programmed instructions, lab results, patient data, configuration information, and rules and clinical protocols to each ventilation system 102 in the hospital 101 in order to configure each ventilation system 102 (e.g., remotely over a wired or wireless network, such as LAN 119). The information provided by the hospital ventilation management system 14 to each ventilation system 102 can be based on the information provided to the hospital ventilation management system 14 by each ventilation system 102.

For example, a ventilation system 102 can provide the hospital ventilation management system 14 with a current configuration profile and current monitor information for a patient associated with the ventilation system 102. The hospital ventilation management system 14 can analyze the information provided by the ventilation system 102 in order to determine which modifications, if any, to make to the configuration profile in view of the patient's monitor information. The hospital ventilation management system 14 may then provide a modified configuration profile to the ventilation system 102 so that the ventilation system 102 may treat the patient in accordance with the modified configuration profile.

The hospital ventilation management system 14 is connected to a wide area ventilation management system 16 configured to manage one or many home ventilation devices 130. Although the hospital ventilation management system 14 and the wide area ventilation management system 16 are illustrated as being separate systems, both the hospital ventilation management system 14 and the wide area ventilation management system 16 can be hosted or otherwise executed from a single server. In certain aspects, many servers may share the hosting responsibilities of the hospital ventilation management system 14 and the wide area ventilation management system 16. The server can be any device having an appropriate processor, memory, and communications capability for hosting the hospital ventilation management system 14 and the wide area ventilation management system 16, and can be in a hospital data center or remotely hosted over a network.

The WAN 120 can include, for example, any one or more of a metropolitan area network (MAN), a wide area network (WAN), a broadband network (BBN), the Internet, and the like. The LAN 119 can include, for example, a personal area network (PAN) or campus area network (CAN). Further, each of the WAN 120 and LAN 119 can include, but is not limited to, any one or more of the following network topologies, including a bus network, a star network, a ring network, a mesh network, a star-bus network, tree or hierarchical network, and the like.

An example use of the ventilator management system will now be provided. A patient associated with the ventilation system 102 is discharged by a clinician 12 from the hospital 101 but still requires ventilation using home ventilation device 130 in the patient's home 140. The hospital ventilation management system 14 registers with the wide area ventilation management system 16, and then sends the patient's information and ventilator information from the ventilation system 102 for the patient to the wide area ventilation management system 16. The home ventilation device 130 is configured using the patient's information and ventilator information and the patient begins treatment using the home ventilation device 130. The clinician monitors the patient's progress with the home ventilation device 130 by reviewing logs from the home ventilation device 130 that are sent to the hospital ventilation management system 14 through the wide area ventilation management system 16. As needed, the clinician may modify the configuration parameters of the home ventilation device 130 remotely by sending new configuration parameters from the hospital ventilation management system 14 to the wide area ventilation management system 16, which then sends the new configuration parameters to the home ventilation device 130 for review by the patient or caregiver. The patient or caregiver accepts the new configuration parameters and the home ventilation device 130 begins to operate according to the new configuration parameters.

Figure 2:
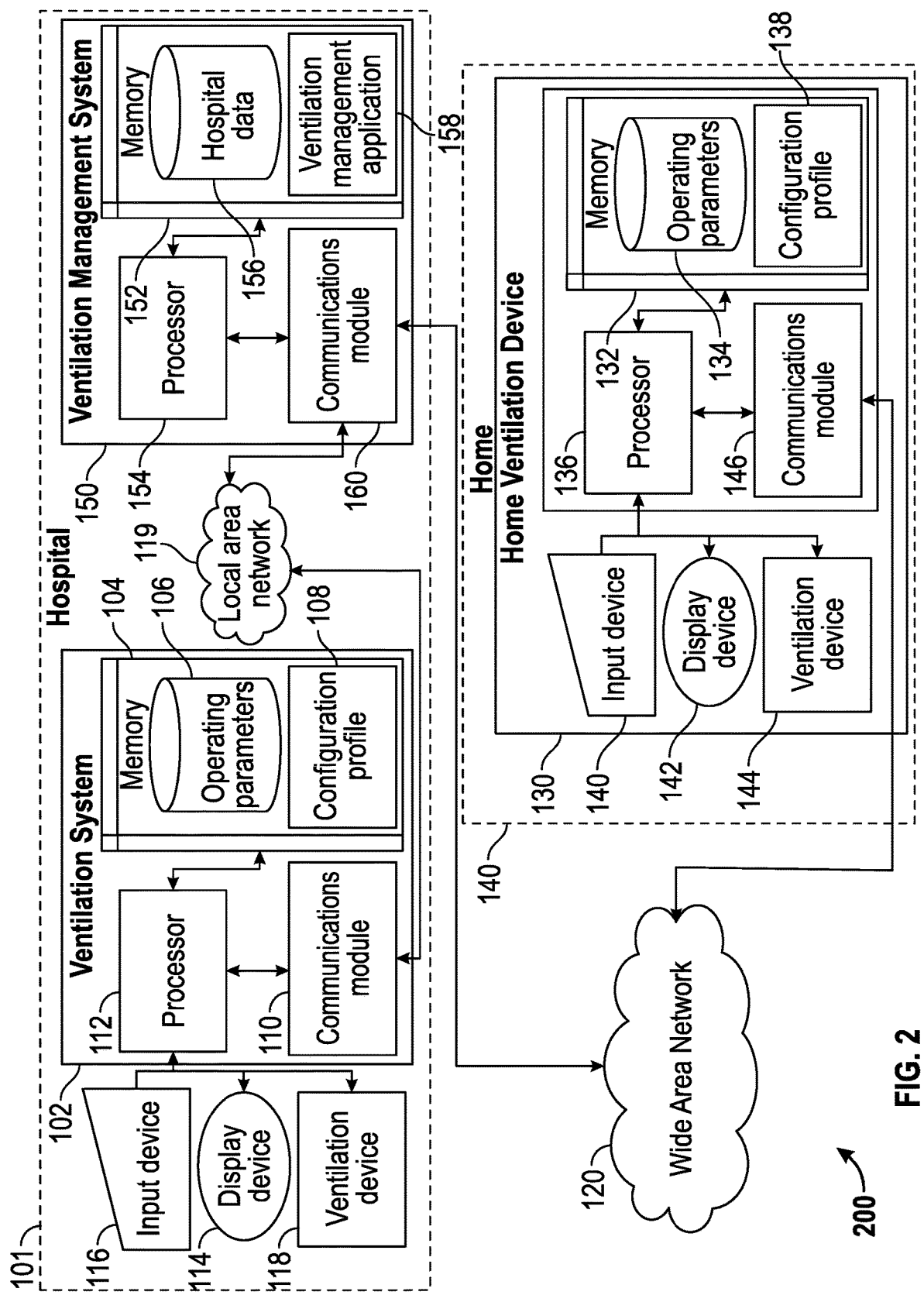
FIG. 2 is a block diagram illustrating an example ventilation system, ventilation management system, and home ventilation device from the architecture of FIG. 1 according to certain aspects of the disclosure.

FIG. 2 is a block diagram illustrating an example ventilation system 102, ventilation management system 150, and home ventilation device 130 from the architecture 10 of FIG. 1 according to certain aspects of the disclosure. Although the ventilation management system 150 is illustrated as connected to a ventilation system 102 and a home ventilation device 130, the ventilation management system 150 is configured to also connect to infusion pumps, point of care vital signs monitors, and pulmonary diagnostics devices.

The ventilation system 102 is connected to the ventilation management system 150 over the LAN 119 via respective communications modules 110 and 160 of the ventilation system 102 and the ventilation management system 150. The ventilation management system 150 is connected over WAN 120 to the home ventilation device 130 via respective communications modules 160 and 146 of the ventilation management system 150 and the home ventilation device 130. The home ventilation device 130 is configured to operate substantially similar to the ventilation system 102 of the hospital 101, except that the home ventilation device 130 is configured for use in the home 140. The communications modules 110, 160, and 146 are configured to interface with the networks to send and receive information, such as data, requests, responses, and commands to other devices on the networks. The communications modules 110, 160, and 146 can be, for example, modems or Ethernet cards.

The ventilation management system 150 includes a processor 154, the communications module 160, and a memory 152 that includes hospital data 156 and a ventilation management application 158. Although one ventilation system 102 is shown in FIG. 2, the ventilation management system 150 is configured to connect with and manage many ventilation systems 102, both ventilation systems 102 for hospitals 101 and home ventilation devices 130 for use in the home 140.

In certain aspects, the ventilation management system 150 is configured to manage many ventilation systems 102 in the hospital 101 according to certain rules and procedures. For example, when powering on, a ventilation system 102 may send a handshake message to the ventilation management system 150 to establish a connection with the ventilation management system 150. Similarly, when powering down, the ventilation system 102 may send a power down message to the ventilation management system 150 so that the ventilation management system 150 ceases communication attempts with the ventilation system 102.

The ventilation management system 150 is configured to support a plurality of simultaneous connections to different ventilation systems 102 and home ventilation devices 130. The number of simultaneous connections can be configured by an administrator in order to accommodate network communication limitations (e.g., limited bandwidth availability). After the ventilation system 102 successfully handshakes with (e.g., connects to) the ventilation management system 150, the ventilation management system 150 may initiate communications to the ventilation system 102 when information becomes available, or at established intervals. The established intervals can be configured by a user so as to ensure that the ventilation system 102 does not exceed an established interval for communicating with the ventilation management system 150.

The ventilation management system 150 can provide the data to the ventilation system 102 in a first-in-first-out (FIFO) order. For instance, if a software upgrade is scheduled to be sent to a ventilation system 102, the software upgrade can be deployed at configurable timeframes in FIFO order for the specified ventilation systems 102. Upon receipt, a ventilation system 102 may initialize the software upgrade on a manual reboot. An admit-discharge-transfer communication can be sent to specified ventilation systems 102 within a certain care area of the hospital 101. A configuration profile communication can be sent to all ventilation systems 102 connected to the ventilation management system 150. On the other hand, orders specific to a patient are sent to the ventilation system 102 associated with the patient.

The ventilation system 102 may initiate a communication to the ventilation management system 150 if an alarm occurs on the ventilation system 102. The alarm may be sent to the beginning of the queue for communicating data to the ventilation management system 150. All other data of the ventilation system 102 may be sent together at once, or a subset of the data can be sent at certain intervals.

The hospital data 156 includes configuration profiles configured to designate operating parameters for the ventilation system 102, operating parameters of the ventilation system 102 and/or physiological statistics of a patient associated with the ventilation system 102. Hospital data 156 also includes patient data for patients at the hospital 101, order (e.g., medication orders, respiratory therapy orders) data for patients at the hospital 101, and/or user data (e.g., for caregivers associated with the hospital 101).

The physiological statistics of the ventilator data includes, for example, a statistic for compliance of the lung (Cdyn, Cstat), flow resistance of the patient airways (Raw), inverse ratio ventilation (I/E), spontaneous ventilation rate, exhaled tidal volume (Vte), total lung ventilation per minute (Ve), peak expiratory flow rate (PEFR), peak inspiratory flow rate (PIFR), mean airway pressure, peak airway pressure, an average end-tidal expired CO2 and total ventilation rate. The operating parameters include, for example, a ventilation mode, a set mandatory tidal volume, positive end respiratory pressure (PEEP), an apnea interval, a bias flow, a breathing circuit compressible volume, a patient airway type (for example endotracheal tube, tracheostomy tube, face mask) and size, a fraction of inspired oxygen (FiO2), a breath cycle threshold, and a breath trigger threshold.

The processor 154 of the ventilation management system 150 is configured to execute instructions, such as instructions physically coded into the processor 154, instructions received from software (e.g., ventilation management application 158) in memory 152, or a combination of both. For example, the processor 154 of the ventilation management system 150 executes instructions to receive ventilator data from the ventilation system 102 (e.g., including an initial configuration profile for the ventilation system 102).

Figure 3:
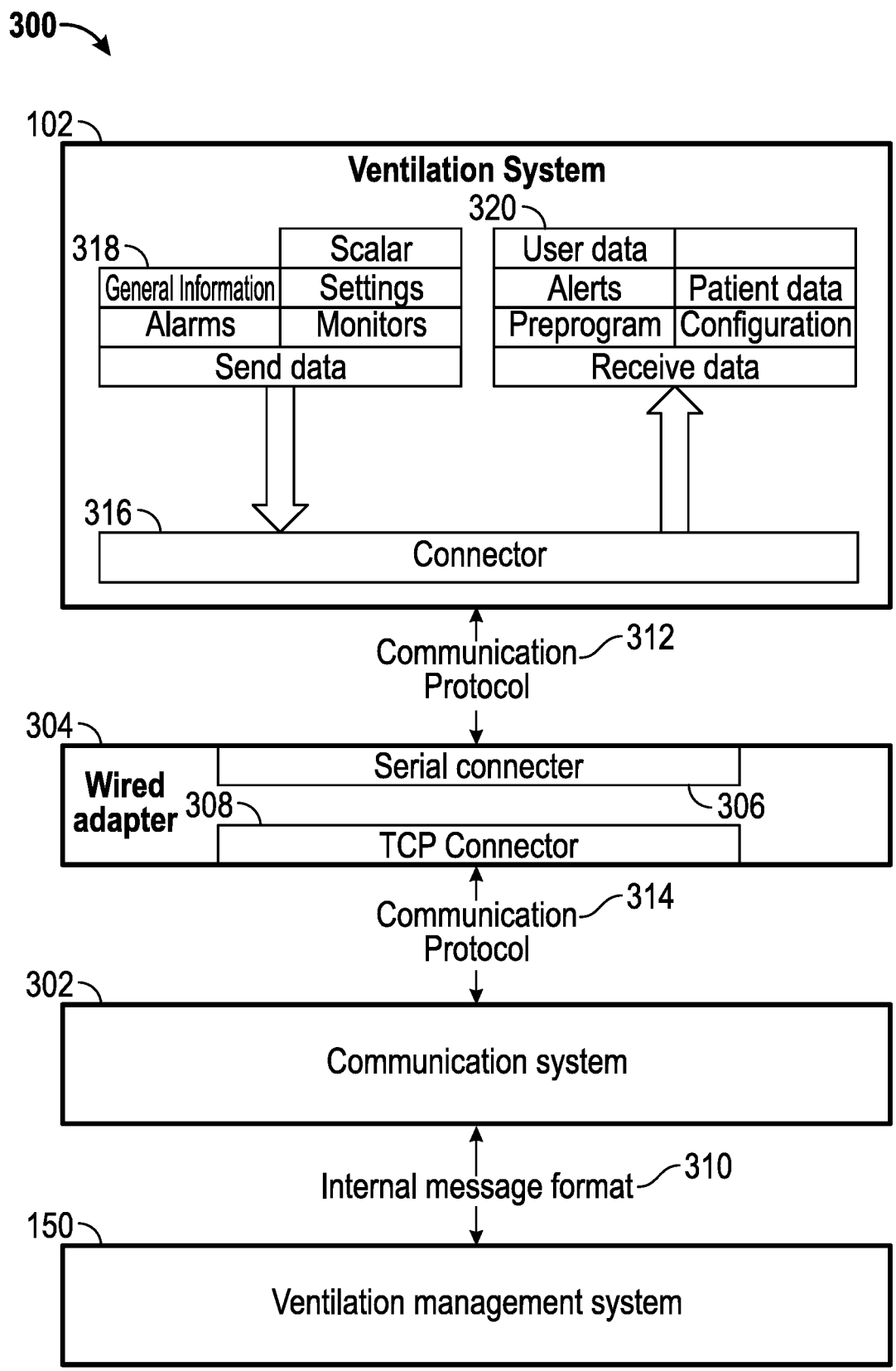
FIG. 3 illustrates an example flow chart of exchanging data between a ventilation system and a ventilation management system.

FIG. 3 illustrates an example flow chart 300 of exchanging data between the ventilation system 102 and the ventilation management system 150. As illustrated in the flow chart 300, the ventilation system 102 is configured to send ventilator information, notifications (or "alarms"), scalars, operating parameters 106 (or "settings"), physiological statistics (or "monitors") of a patient associated with the ventilation system 102, and general information. The notifications include operational conditions of the ventilation system 102 that may require operator review and corrective action. The scalars include parameters that are typically updated periodically (e.g., every 500 ms) and can be represented graphically on a two-dimensional scale. The physiological statistics represent information that the ventilation system 102 is monitoring, and can dynamic based on a specific parameter. The operating parameters 106 represent the operational control values that the caregiver has accepted for the ventilation system 102. The general information can be information that is unique to the ventilation system 102, or that may relate to the patient (e.g., a patient identifier). The general information can include an identifier of the version and model of the ventilation system 102.

Figure 4:
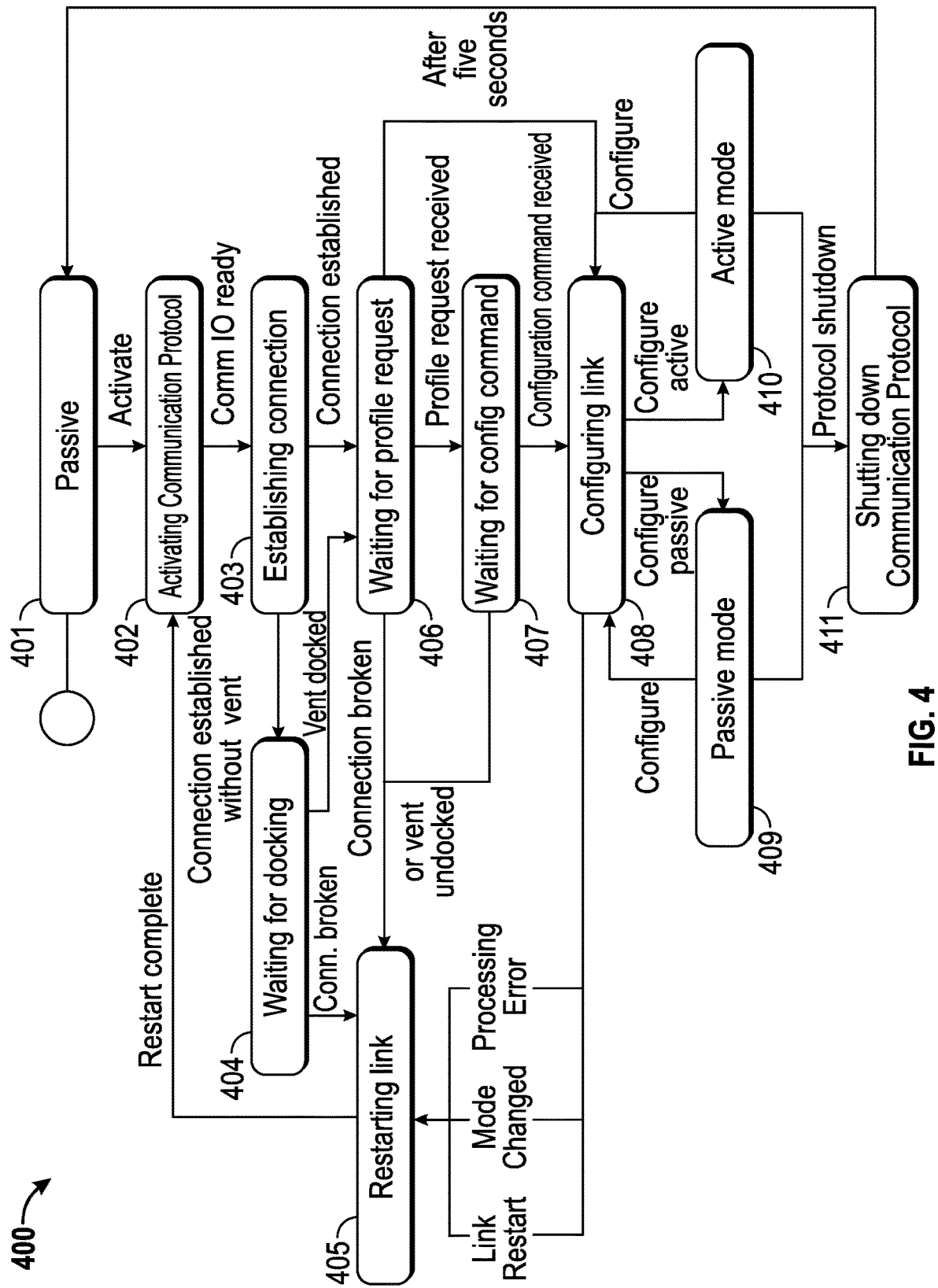
FIG. 4 illustrates an example flow chart for a communication protocol used by the ventilation system of FIG. 3.

In the example of FIG. 3, the data is sent via a serial connector. The data is sent to a wired adapter 304 having a serial connector and a TCP connector 308. The data is sent using any appropriate communication protocol 400 (e.g., VOXP protocol). FIG. 4 illustrates an example flow chart for a communication protocol, the VOXP protocol, used by the ventilation system 102 of FIG. 3.

The communication protocol 400 of FIG. 4 is configured, in certain aspects, to operate in an active mode and a passive mode. In active mode, the ventilation system 102 both responds to requests (e.g., from the ventilation management system 150), as well as automatically sends data as it becomes available to the ventilation system 102. In passive mode, the ventilation system 102 responds to requests but does not automatically send data as it becomes available. The protocol 400 begins by transition from a dormant (or "passive") mode 401 to starting the VOXP protocol 402 (e.g., to enter into active mode). When the communication input/output port is ready, a connection is established 403 with the destination (e.g., wired adapter 304). If the connection is established without a ventilation device 118 being connected to the ventilation system 102, then the protocol instructs to wait for docking 404 (e.g., of a ventilation device 118). If a connection is broken while waiting for docking, the link between the ventilation system 102 and the destination is reestablished 405. Otherwise, when a ventilation device 118 is docked, or a connection is established, the protocol waits for a profile or other data request 406 (e.g., from the ventilation management system 150). If the connection is broken while waiting for the profile request, the link between the ventilation system 102 and the destination is reestablished. When the profile request is received, ventilation system 102 sends a configuration profile 108 (specifying the capabilities of the ventilation system 102 and the set of operating parameters and other data that it can provide), and then the protocol waits for a configuration command 407 (e.g., from the ventilation management system 150). When the configuration command is received, a link is established with the destination and the link is configured 408. If while configuring the link there is a processing error, a mode changes, or the link is restarted, the link is again reestablished 405. Otherwise, upon configuring the link 408, the protocol for the ventilation system 102 may enter a passive mode 409 or active mode 410. In passive mode 409, the ventilation management system 150 sends requests, at intervals determined by the ventilation management application 158, for specified information. At each such request, the ventilation system 102 responds with the specified information 318, which may include notifications (or "alarms"), scalars, operating parameters 106 (or "settings"), and physiological statistics (or "monitors") of a patient associated with the ventilation system 102. In active mode 410, the ventilation system 102 sends specified information 318, which may include notifications (or "alarms"), scalars, operating parameters 106 (or "settings"), and physiological statistics (or "monitors") of a patient associated with the ventilation system 102, as each item becomes available. For example an operating parameter 106 is sent when a user of the ventilation system makes a change to a set value. When the ventilation system is turned off, the protocol signals a shutdown 411. Upon shutting down, the protocol can automatically enter a dormant mode 401 (e.g., after 5 seconds).

Returning to FIG. 3, the wired adapter 304 is configured to receive 312 the data according to the communication protocol 400 of FIG. 4, and convert the data from a serial connection format to a TCP connection format. The wired adapter 304 then provides 314 the data in the TCP connection format according to the communication protocol 400 of FIG. 4 to a communication system 302.

The data is received from the ventilation system 102 through the wired adapter 304 by the communication system 302. The data may be in a native message format of the ventilation system 102. The communication system 302 is configured to convert the data into an internal messaging format configured for use with a ventilation management system 150. The conversion can take place according to the system and method of converting messages being sent between data systems using different communication protocols and message structures described in U.S. patent application Ser. No. 13/421,776, entitled "Scalable Communication System," and filed on Mar. 15, 2012, the disclosure of which is hereby incorporated by reference in its entirety for all purposes. The communication system 302 can include, for example, an interface module for communicating with the wired adapter 304.

The interface module can include information on the communication protocol 400 (e.g., VOXP protocol) and data structure used by the ventilation system 102 and is configured to both receive messages from and transmit messages between the ventilation system 102 and the ventilation management system 150. For example, the ventilation management system 150 is configured to provide, through the communication system 302 and the wired adapter 304, patient data, order data, configuration data, user data, pre-programmed information, vital sign information, rules, notifications, and clinical protocols to the ventilation system 102. The patient data includes, for example, admit-discharge-transfer data, allergy data, diagnosis data, medication history, procedure history, a patient's name, the patient's medical record number (MRN), lab results, or the patient's visit number. Medication history may include a list of the medications and doses that have been administered to the patient, for example sedative medications, muscle paralytic medications, neural block medications, anti-inflammatory medications. Procedure history may include a list of surgical or other interventional procedures that have been administered, for example cardiothoracic surgery; lung lavage; maxillofacial surgery; chest physiotherapy. The order data includes, for example medication order information, procedure order information for at least one of physical therapy or percussion therapy, sedation order information indicating sedation vacations or modes of ventilator therapy, therapy order information for invasive or non-invasive ventilator therapy, or trial order information for spontaneous breathing trials. The configuration data includes, for example, a patient profile, a user interface configuration, a limit configuration, a notification configuration, or a clinical protocol configuration. The notification configuration can indicate whether certain limits or alerts should be enabled or disabled, and the clinical protocol configuration can be used in a particular area of the hospital 101 (e.g., ICU) and indicate which clinical protocol library should be enabled. A clinical protocol library may include several clinical protocols that may be applicable to a specified group of patients, for example a spontaneous breathing trial clinical protocol. A clinical protocol may include a set of rules defining actions that the ventilation system 102 should effect in response to events such as a change in patient physiological data, for example a spontaneous breathing trial clinical protocol may include a rule that recommences mandatory ventilation in the event that the patient's rapid shallow breathing index (RSBI) exceeds a set threshold. As another example the spontaneous breathing trial clinical protocol may include a rule that a notification should be provided on display device 114 when the patient has been controlling their own respiration within specified limits for a period of one hour. In certain aspects, the notifications can be generated by the ventilation management system 150 and sent to the ventilation system 102 to alert a caregiver or patient near the ventilation system 102. The user data includes, for example, an identification of a caregiver or a healthcare institution.

After receiving the ventilator data from the ventilation system 102, the processor 154 of the ventilation management system 150 is configured to determine, based on the ventilator data, a modification to the initial configuration profile for the ventilation system 102. In certain aspects, the initial configuration profile is received by the ventilation management system 150 from the ventilation system 102. The processor 154 of the ventilation management system 150 is further configured to generate a modified configuration profile for the ventilation system 102 based on the determined modification. In certain aspects, the modification to the configuration profile is also determined based on the initial configuration profile of the ventilation system 102. For example, if the initial configuration profile indicated an average end tidal CO2 level that was considered clinically too low for the patient, the configuration profile could be modified to increase the average end tidal CO2.

In certain aspects, the modification to the configuration profile is also determined based on comparing the physiological statistics of the patient with historical patient data (e.g., stored in the hospital data 156) to identify a modification to at least one operating parameter of the initial configuration profile, and modify the operating parameter based on the identification. For example, if an apnea interval that, based on historical patient data for many patients at the hospital 101, was not likely to improve the condition of the patient, then the apnea interval of the configuration profile could be modified by the ventilation management system 150. As another example, if a specified level of tidal ventilation normalized to patient weight, based on historical patient data for many patients at the hospital 101 with a specified diagnosis, has been associated with a reduced length of hospital stay, then the configuration profile could be modified to adjust pressure support to target this level of tidal ventilation.

The processor 154 of the ventilation management system 150 can be further configured to provide the modified configuration profile to the ventilation system 102 for modifying operating parameters 106 in the memory 104 of the ventilation system 102. The modified configuration profile 108 is stored in the memory 104 of the ventilation system, and used by the processor 112 of the ventilation system 102 to modify the operating parameters 106 in the memory 104 of the ventilation system. In certain aspects, details regarding the modified configuration profile (e.g., the modifications made to operating parameters, an identification of a clinician responsible for approving the modifications, etc.) are provided for display using the display device 114 of the ventilation system 102.

The ventilation system 102 includes a processor 112, the communications module 110, and a memory 104 that includes operating parameters 106 and a configuration profile 108. The ventilation system 102 also includes an input device 116, such as a keyboard, scanner, or mouse, an output device 214, such as a display, and a ventilation device 118 configured to mechanically move breathable air into and out of lungs in order to assist a patient in breathing according to instructions from the ventilation system 102. The configuration profile 108 includes one or many configuration profiles for operating the ventilation device 118 of the ventilation system 102. For example, the configuration profile 108 can include a profile for operating the ventilation device 118 in an intensive care unit, neonatal intensive care unit, or surgical room, or a profile for operating the ventilation device 118 for patients with a specified respiratory diagnosis, such as ARDS, neuromuscular disease, pneumonia, or post-surgical recovery.

The processor 112 of the ventilation system 102 is configured to execute instructions, such as instructions physically coded into the processor 112, instructions received from software (e.g., from configuration profile 108) in memory 104, or a combination of both. For example, the processor 112 of the ventilation system 102 executes instructions to configure the ventilation device 118. The processor 112 of the of the ventilation system 102 executes instructions from the configuration profile 108 causing the processor 112 to receive, over the LAN 119, at least one of patient data, order data, configuration data, or user data. The configuration data can include, for example, an indication (e.g., a set limit) for limiting use of the ventilation system 102 within the hospital 101. The processor 112 of the of the ventilation system 102 is also configured to provide a modification of operating parameters 106 of the ventilation device 118 based on the received patient data, order data, configuration data, or user data.

Figure 5:
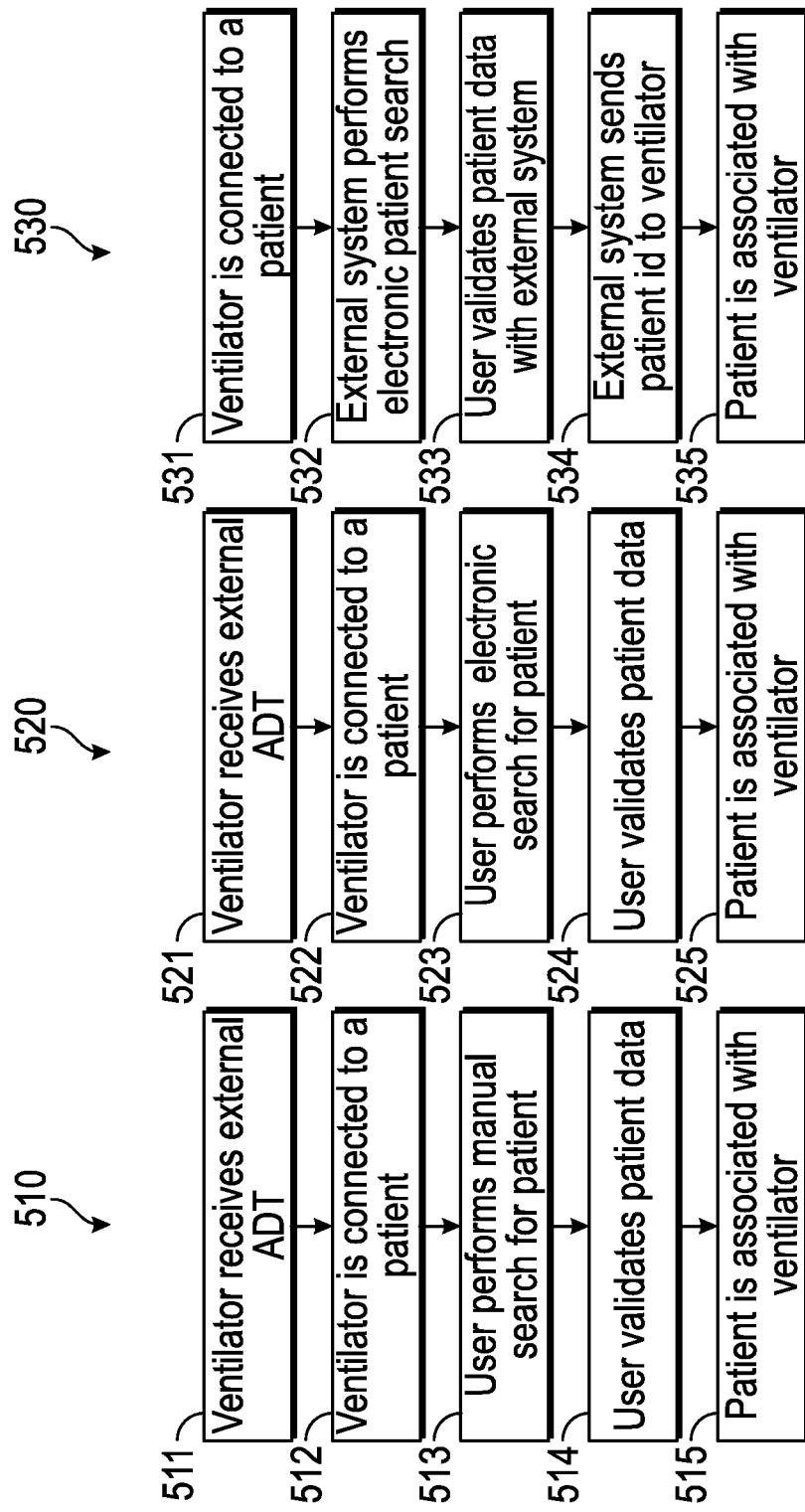
FIG. 5 illustrates example processes for contextualizing ventilator data for a ventilation system.

In certain aspects the patient data received by the ventilation system 102 includes a patient identifier, such as a MRN, that is obtained through various processes 510, 520, and 530 and used to contextualize data generated by the ventilation system 102 as illustrated in FIG. 5. The contextualization of data includes identifying data generated by a ventilation system 102 as being data associated with a specific patient (a "patient context"). The patient context and ventilation system 102 to patient association can be stored in the memory 103 of the ventilation system 102 or in the hospital data 156 in the memory 152 of the ventilation management system 150.

As provided in process 510 of FIG. 5, a ventilation system 102 can be associated with a patient manually when the ventilation system 102 first receives in step 511 an external admit-discharge-transfer alert (e.g., from the ventilation management system 150 or a hospital information system) for a patient. Next, in step 512, the ventilation system 102 is connected to the patient and in step 513 a caregiver, using input device 116 and display device 114, searches for the patient's name or identifier (from among a list of patient names/identifiers) on the display device 114 of the ventilation system 102. The patient's identifier can be found, for example, using a search by care area, patient type, alphabetically, or a list of patients associated with the caregiver. In step 514, the user validates the patient data (e.g., selects the patient to associate with the ventilation system 102) and in step 515 the patient is associated with the ventilation system 102. In certain aspects, a second identifier can be required, such as a medical record number, in order to validate the patient data.

As provided in process 520 of FIG. 5, a ventilation system 102 can be associated with a patient automatically when the ventilation system 102 again first receives in step 521 an external admit-discharge-transfer alert (e.g., from the ventilation management system 150 or a hospital information system) for a patient and the ventilation system 102 is connected to the patient in step 522. Next, in step 523, a clinician performs an electronic search for the patient by, for example, scanning a barcode on the patient's wrist with the input device 116 or having the ventilation system 102 identify the patient using a radio frequency identification (RFID). Next, in step 524, the user validates the patient data (e.g., confirms the automatically identified patient) and in step 525 the patient is associated with the ventilation system 102.

As provided in process 530 of FIG. 5, a ventilation system 102 can also be associated with a patient automatically when the ventilation system 102 is connected to a patient in step 531 and an external system (e.g., a network scanner connected to a server, such as the ventilation management system 150 or an admit-discharge-transfer system) performs a search for the patient (e.g., using RFID). The user in step 533 validates the patient data identified by the external system and the external system sends the patient identification to the ventilation system 102 in step 534. In step 535 the patient is associated with the ventilation system 102. As yet another example, a ventilator may first be connected to a patient, the ventilation system 102 or user then performs an electronic search by, for example, and RFID or scanned patient barcode, the external system validates patient data, the external system sends patient data to the ventilation system 102, and the patient is associated with the ventilation system 102.

In certain aspects, both the ventilation management system 150 and ventilation system 102 are configured to cache data, such as the patient data, order data, configuration data, user data, vital sign information (e.g., physiological statistics of a patient), rules, notifications, clinical protocols, and operating parameters. Cached (or "logged") data can be used to perform analytics that result in improved patient care. By caching the data even when the ventilation system 102 or the ventilation management system 150 are not connected, the data will have a greater chance of being used for analytics and result in improved patient care. The data may be cached, for example, when the LAN 119 connection is unavailable. The data may then be shared between the ventilation management system 150 and ventilation system 102 when the connection becomes available. Similarly, the data may then be shared between the ventilation management system 150 and ventilation system 102 at regularly scheduled intervals (e.g., every 30 minutes). The scheduled intervals are configurable by a caregiver or other user, and can be based on, for example, the data being transmitted, when a change is made to an operating parameter of the ventilation system 102, or when a measured value, alarm threshold, or monitored value reach a predefined level or rate of change. The home ventilation device 130 can also cache data similar to the ventilation system 102. The data may be cached by the home ventilation device 130, for example, when the WAN 120 connection is unavailable.

For example, any data that is generated by the ventilation system 102 for documentation, clinical decision support, biomedical engineering or maintenance support can be cached in the memory 104 of the ventilation system 102 to be sent out to the ventilation management system 150. Similarly, any data that needs to be sent to the ventilation system 102 from the ventilation management system 150 can be cached in memory 152 at the ventilation management system 150 until a scheduled time to send the data, or a next time the ventilation system 150 and ventilation are connected.

Figure 6:
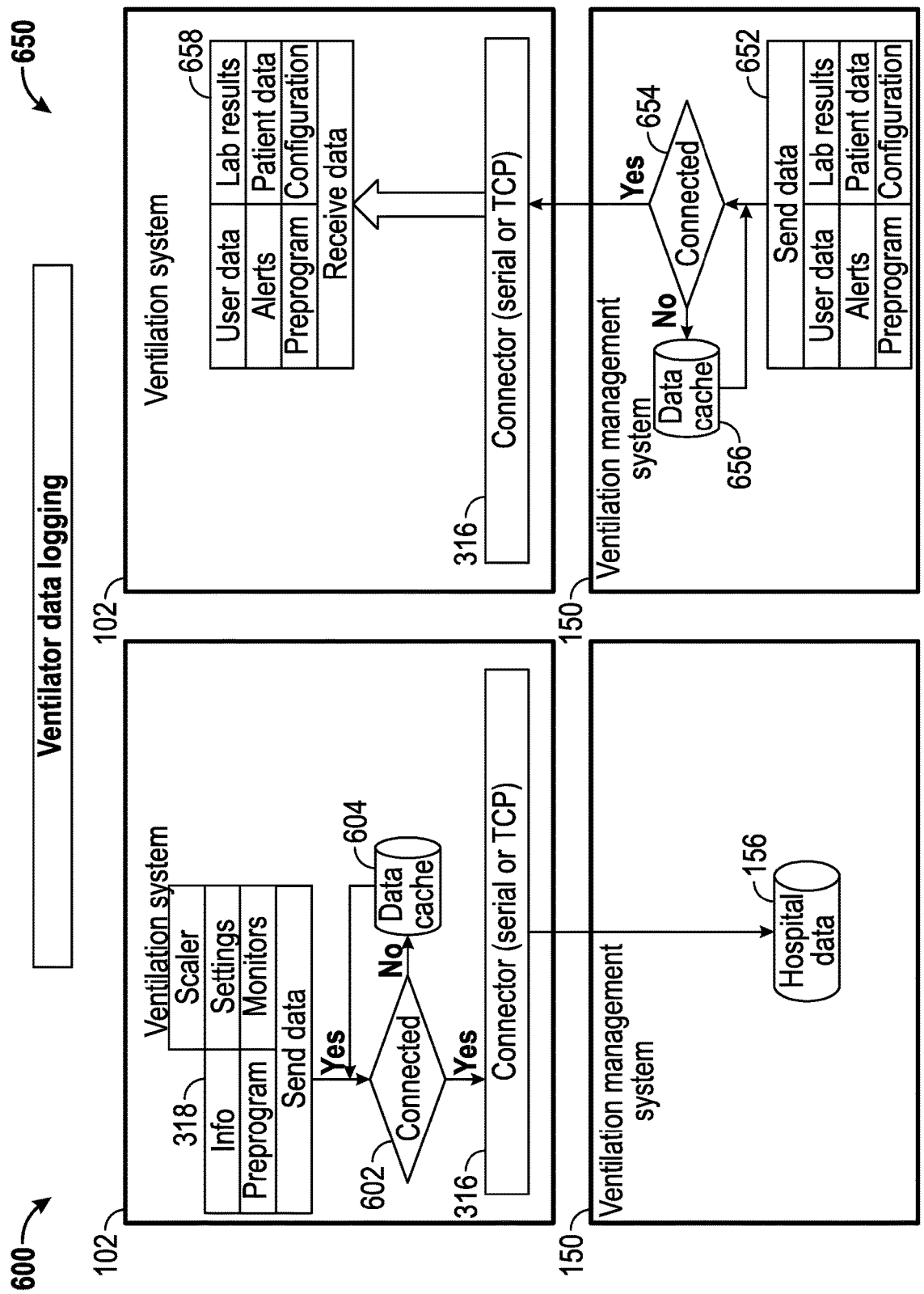
FIGS. 6A and 6B illustrate example flow charts for caching data on a ventilation system and a ventilation management system.

FIGS. 6A and 6B illustrate example flow charts for caching data on a ventilation system 102 and a ventilation management system 150. In FIG. 6A, data 318 for the ventilation system 102, including ventilation system information, alarms, scalars, settings, and monitors, when available, is sent to the ventilation management system 150 via a connector 316 for storage as hospital data 156 when a connection 602 between the ventilation system 102 and the ventilation management system 150 is available. Otherwise, when the connection 602 between the ventilation system 102 and the ventilation management system 150 is not available, the data is stored in a data cache 604 on the ventilation system 102.

In FIG. 6B, data 652 for the ventilation management system 150, including user data, alerts, preprogrammed information, lab results, patient data, and configuration information, when available, is sent to the ventilation system 102 via a connector 316 for storage as data 658 in memory 104 when a connection 654 between the ventilation system 102 and the ventilation management system 150 is available. Otherwise, when the connection 654 between the ventilation system 102 and the ventilation management system 150 is not available, the data is stored in a data cache 656 on the ventilation management system 150.

Figure 7:
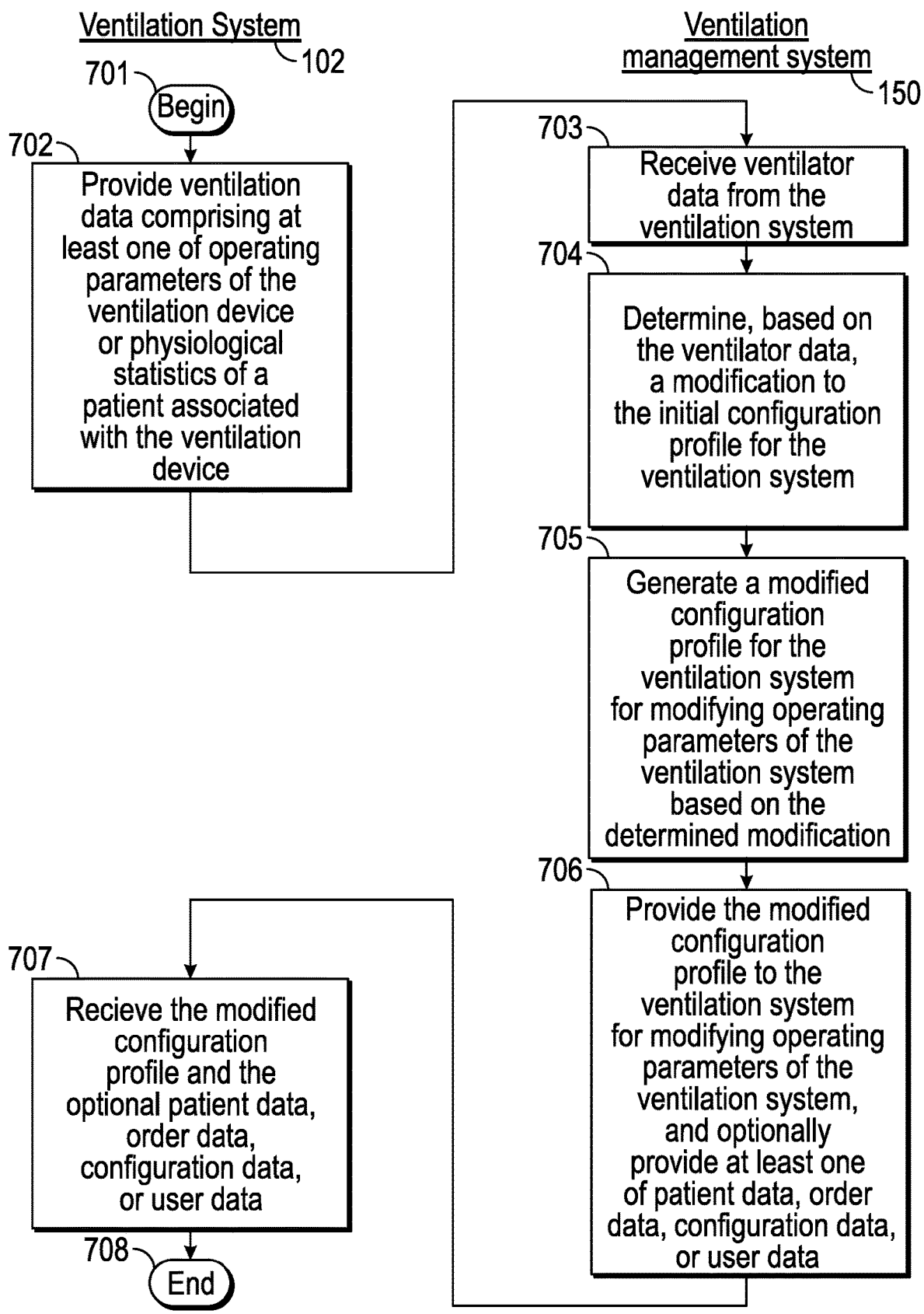
FIG. 7 illustrates an example process for managing a ventilation system.

FIG. 7 illustrates an example process 700 for managing a ventilation system using the example ventilation system 102 and ventilation management system 150 of FIG. 2. While FIG. 7 is described with reference to FIG. 2, it should be noted that the process steps of FIG. 7 may be performed by other systems.

The process 700 begins by proceeding from beginning step 701 when a ventilation system 102 is initialized and establishes a communication with the ventilation management system 150, to step 702 when the ventilation system 102 provides ventilator data including at least one of operating parameters of the ventilation device 118 or physiological statistics of a patient associated with the ventilation device 118 to the ventilation management system 150. In step 703, the ventilation management system 150 receives the ventilator data from the ventilation system 102 and in step 704 determines, based on the ventilator data, a modification to the initial configuration profile 108 for the ventilation system 102. In step 705 a modified configuration profile is generated for the ventilation system 102 based on the determined modification of step 704, and in step 706 the ventilation management system 706 provides the modified configuration profile to the ventilation system 102 for modifying the operating parameters 106 of the ventilation system 102. The ventilation management system 706 may also optionally provide at least one of patient data, order data, configuration data, or user data to the ventilation system 102 in step 706. In step 707, the ventilation system 102 receives the modified configuration profile and optional patient data, order data, configuration data, or user data. The process 700 then ends in step 708.

FIG. 7 sets forth an example process 700 for managing a ventilation system using the example ventilation system 102 and ventilation management system 150 of FIG. 2. An example will now be described using the example process 700 of FIG. 7.

The process 700 begins by proceeding from beginning step 701 when a ventilation system 102 in the hospital 101 is turned on and establishes a communication with the ventilation management system 150, to step 702 when the ventilation system 102 provides operating parameters of the ventilation device 118, physiological statistics of a patient associated with the ventilation device 118, and an initial configuration profile 108 of the ventilation system 102 to the ventilation management system 150. In step 703, the ventilation management system 150 receives the data from the ventilation system 102 and in step 704 determines that the patient's tidal volume has decreased over the last five minutes by 30%, which is an indication of a degradation in the patient's clinical status. The data also indicates the patient's heart rate has increased. The ventilation management system 150 further determines, based on the ventilator data, that the initial configuration profile 108 for the ventilation system 102 should be modified to increase the breath rate parameter. In an alternative example, in step 704 the ventilation management system 150 uses data from other devices such as lab results data 652 including a blood oxygen measurement and a blood carbon dioxide measurement which indicate that the patient is being over-ventilated. The ventilation management system 150 further determines, based on the lab results data, that the initial configuration profile 108 for the ventilation system 102 should be modified to decrease the breath rate parameter. In step 705 the modified configuration profile having the changed breath rate parameter is generated for the ventilation system 102 based on the determined modification of step 704, and in step 706 the ventilation management system 706 provides the modified configuration profile to the ventilation system 102 for modifying the operating parameters 106 of the ventilation system 102. The configuration profile 108 of the ventilation system 102 is modified with the modified configuration profile to increase the patient's breath rate, and the process 700 then ends in step 708.

Figure 8:
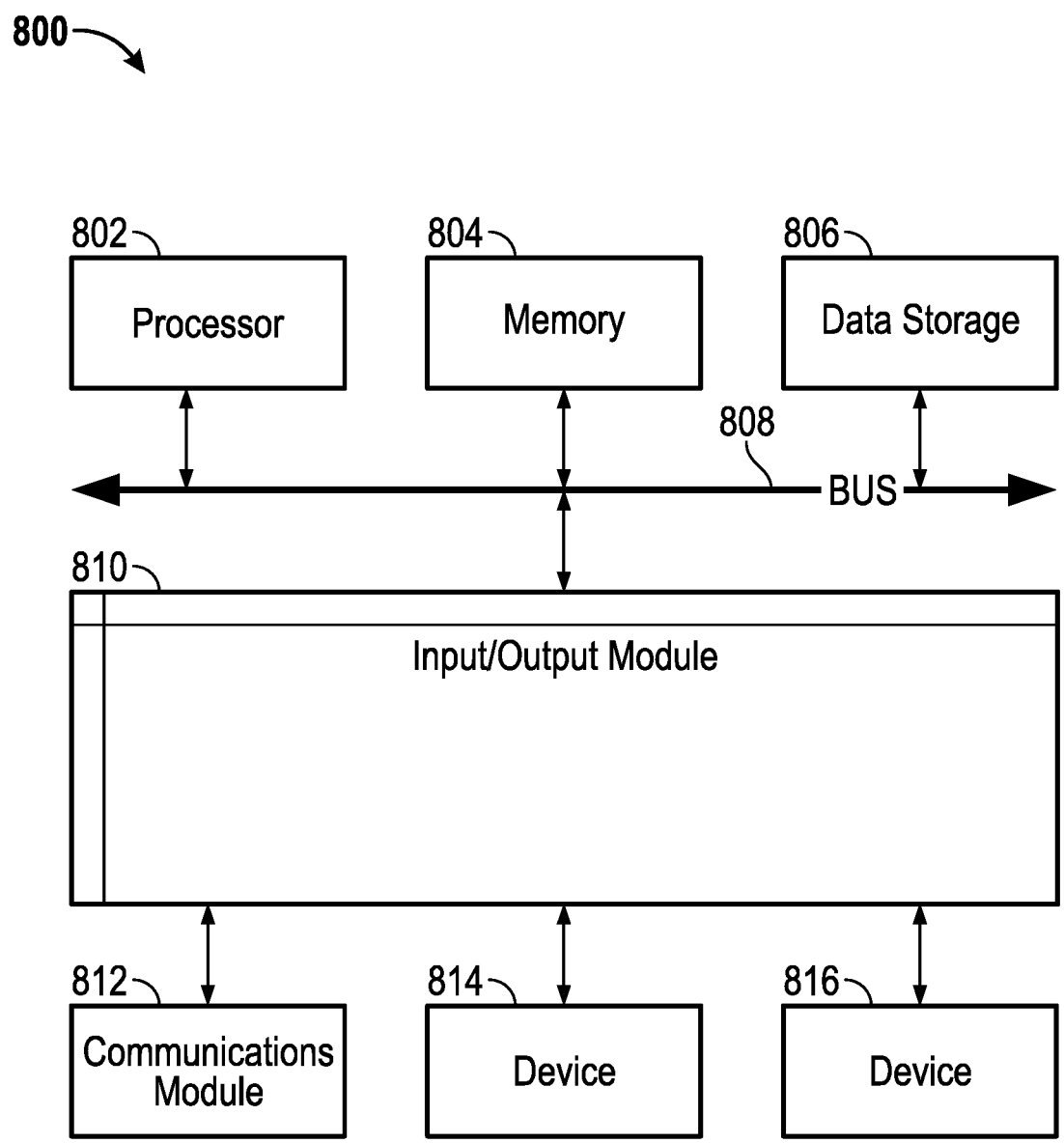
FIG. 8 is a block diagram illustrating an example computer system with which the example ventilation system, ventilation management system, and home ventilation device of FIG. 2 can be implemented.

FIG. 8 is a block diagram illustrating an example computer system 800 with which the ventilation system 102, ventilation management system 150, and home ventilation device 130 of FIG. 2 can be implemented. In certain aspects, the computer system 800 may be implemented using hardware or a combination of software and hardware, either in a dedicated server, or integrated into another entity, or distributed across multiple entities.

Computer system 800 (e.g., ventilation system 102, ventilation management system 150, and home ventilation device 130) includes a bus 808 or other communication mechanism for communicating information, and a processor 802 (e.g., processor 112, 154, and 136) coupled with bus 808 for processing information. By way of example, the computer system 800 may be implemented with one or more processors 802. Processor 802 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information.

Computer system 800 can include, in addition to hardware, code that creates an execution environment for the computer program in question, e.g., code that constitutes processor firmware, a protocol stack, a database management system, an operating system, or a combination of one or more of them stored in an included memory 804 (e.g., memory 104, 152, and 132), such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 808 for storing information and instructions to be executed by processor 802. The processor 802 and the memory 804 can be supplemented by, or incorporated in, special purpose logic circuitry.

The instructions may be stored in the memory 804 and implemented in one or more computer program products, i.e., one or more modules of computer program instructions encoded on a computer readable medium for execution by, or to control the operation of, the computer system 800, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, embeddable languages, and xml-based languages. Memory 804 may also be used for storing temporary variable or other intermediate information during execution of instructions to be executed by processor 802.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 800 further includes a data storage device 806 such as a magnetic disk or optical disk, coupled to bus 808 for storing information and instructions. Computer system 800 may be coupled via input/output module 810 to various devices (e.g., ventilation device 118). The input/output module 810 can be any input/output module. Example input/output modules 810 include data ports such as USB ports. The input/output module 810 is configured to connect to a communications module 812. Example communications modules 812 (e.g., communications modules 110, 160, and 146) include networking interface cards, such as Ethernet cards and modems. In certain aspects, the input/output module 810 is configured to connect to a plurality of devices, such as an input device 814 (e.g., input device 116) and/or an output device 816 (e.g., display device 114). Example input devices 814 include a keyboard and a pointing device, e.g., a mouse or a trackball, by which a user can provide input to the computer system 800. Other kinds of input devices 814 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Example output devices 816 include display devices, such as a LED (light emitting diode), CRT (cathode ray tube), or LCD (liquid crystal display) screen, for displaying information to the user.

According to one aspect of the present disclosure, the ventilation system 102, ventilation management system 150, and home ventilation device 130 can be implemented using a computer system 800 in response to processor 802 executing one or more sequences of one or more instructions contained in memory 804. Such instructions may be read into memory 804 from another machine-readable medium, such as data storage device 806. Execution of the sequences of instructions contained in main memory 804 causes processor 802 to perform the process steps described herein. One or more processors in a multi-processing arrangement may also be employed to execute the sequences of instructions contained in memory 804. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. The communication network (e.g., local area network 119 and wide area network 120) can include, for example, any one or more of a personal area network (PAN), a local area network (LAN), a campus area network (CAN), a metropolitan area network (MAN), a wide area network (WAN), a broadband network (BBN), the Internet, and the like. Further, the communication network can include, but is not limited to, for example, any one or more of the following network topologies, including a bus network, a star network, a ring network, a mesh network, a star-bus network, tree or hierarchical network, or the like. The communications modules can be, for example, modems or Ethernet cards.

Computing system 800 can include clients and servers. A client and server are generally remote from each other and typically interact through a communication network. The relationship of client and server arises by virtue of computer programs running on the respective computers and having a client-server relationship to each other. Computer system 800 can be, for example, and without limitation, a desktop computer, laptop computer, or tablet computer. Computer system 800 can also be embedded in another device, for example, and without limitation, a mobile telephone, a personal digital assistant (PDA), a mobile audio player, a Global Positioning System (GPS) receiver, a video game console, and/or a television set top box.

The term "machine-readable storage medium" or "computer readable medium" as used herein refers to any medium or media that participates in providing instructions or data to processor 802 for execution. Such a medium may take many forms, including, but not limited to, non-volatile media, volatile media, and transmission media. Non-volatile media include, for example, optical disks, magnetic disks, or flash memory, such as data storage device 806. Volatile media include dynamic memory, such as memory 804. Transmission media include coaxial cables, copper wire, and fiber optics, including the wires that comprise bus 808. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim.

A reference to an element in the singular is not intended to mean "one and only one" unless specifically stated, but rather "one or more." All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The subject matter of this specification has been described in terms of particular aspects, but other aspects can be implemented and are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other variations are within the scope of the following claims.

These and other implementations are within the scope of the following claims.

What is claimed is:

1. A ventilator management system, comprising:
a memory storing an initial configuration profile including a set of operating parameters for operating one or more respective ventilation devices; and
one or more processors configured to:
receive, over a network, first ventilator data from a first ventilation device at a first location, and second ventilator data from a second ventilation device at a second location, the first and second ventilation devices being configured to operate based on the initial configuration profile, wherein the received first ventilator data comprises one or more current operating parameters of the first ventilation device, or physiological data obtained from a patient associated with the first ventilation device;
modify the initial configuration profile for use by the first ventilation device based on the received first ventilation data; and
provide, over the network, the modified configuration profile to the first ventilation device,
wherein the modified configuration profile is configured to be implemented by the first ventilation device after the modified configuration profile is provided to and accepted by the patient associated with the first ventilation device.

2. The ventilator management system of claim 1, wherein modifying the initial configuration profile includes modifying one or more initial operating parameters of the initial configuration profile.

3. The ventilator management system of claim 2, wherein the one or more processors are further configured to:
determining, based on the first ventilation data, that a physiological parameter of the patient has changed over a period of time to indicate a degradation in a clinical status of the patient; and
modifying an operating parameter associated with a breath rate,
wherein the modified configuration profile is configured to cause the first ventilation device to adjust a ventilation of the patient based on the modified operating parameter associated with the breath rate.

4. The ventilator management system of claim 3, wherein the physiological parameter includes a tidal volume or heart rate.

5. The ventilator management system of claim 2, wherein the one or more processors are further configured to:
receiving a physiological parameter associated with the patient from an external device, different than the first or second ventilation device;
determining, based on the physiological parameter, that the patient is not receiving a correct amount of ventilation;
modifying, responsive to determining that the patient is not receiving the correct amount of ventilation, an operating parameter associate with a breath rate,
wherein the modified configuration profile is configured to cause the first ventilation device to adjust an amount of ventilation provided to the patient based on the modified operating parameter associated with the breath rate.

6. The ventilator management system of claim 5, wherein the physiological parameter includes a blood oxygen measurement or a blood carbon dioxide measurement indicating that the patient is being over-ventilated.

7. The ventilator management system of claim 1, wherein the initial configuration profile is modified for the first ventilation device based on the first ventilation data received from the first ventilation device and the second ventilation data received from the second ventilation device.

8. The ventilator management system of claim 1, wherein the one or more processors are further configured to:
receive the initial configuration profile from the first ventilation device before receiving the first ventilator data from the first ventilation device,
wherein the initial configuration profile received from the first ventilation device is modified based on the received first ventilation data.

9. The ventilator management system of claim 1, wherein the one or more processors are further configured to:
compare the first ventilation data with historical patient data associated with a plurality of patients; and
modify the initial configuration profile based on the comparing of the first ventilation data with the historical patient data associated with a plurality of patients.

10. The ventilator management system of claim 9, wherein the first ventilation data includes the physiological data obtained from the patient associated with the first ventilation device, and wherein the initial configuration profile is modified based on comparing the physiological data with the historical patient data associated with a plurality of patients.

11. The ventilator management system of claim 1, wherein the first ventilation data includes the one or more current operating parameters and the physiological data,
wherein the one or more current operating parameters comprises at least one of a ventilation mode, a set mandatory tidal volume, a set positive end respiratory pressure (PEEP), an apnea interval, a bias flow, a breathing circuit compressible volume, a patient airway type and size, a fraction of inspired oxygen (FiO2), a breath cycle threshold, or a breath trigger threshold, and
wherein the physiological data comprising at least one of a statistic for compliance of a lung (Cdyn, Cstat), resistance of a patient airway (Raw), inverse ratio ventilation (I/E), spontaneous ventilation rate, exhaled tidal volume (Vte), total lung ventilation per minute (Ve), peak expiratory flow rate (PEFR), peak inspiratory flow rate (PIFR), mean airway pressure, peak airway pressure, an average end-tidal expired CO2 or total ventilation rate.

12. A method for managing a plurality of ventilators, the method comprising:
storing an initial configuration profile including a set of operating parameters for operating one or more respective ventilation devices;
receiving, over a network, first ventilator data from a first ventilation device at a first location, and second ventilator data from a second ventilation device at a second location, the first and second ventilation devices being configured to operate based on the initial configuration profile, wherein the received first ventilator data comprises one or more current operating parameters of the first ventilation device, or physiological data obtained from a patient associated with the first ventilation device;
modifying the initial configuration profile for use by the first ventilation device based on the received first ventilation data; and
providing, over the network, the modified configuration profile to the first ventilation device,
wherein the modified configuration profile is configured to be implemented by the first ventilation device after the modified configuration profile is provided to and accepted by the patient associated with the first ventilation device.

13. The method of claim 12, wherein modifying the initial configuration profile includes modifying one or more initial operating parameters of the initial configuration profile.

14. The method of claim 13, further comprising:
determining, based on the first ventilation data, that a physiological parameter of the patient has changed over a period of time to indicate a degradation in a clinical status of the patient; and
modifying an operating parameter associated with a breath rate,
wherein the modified configuration profile is configured to cause the first ventilation device to adjust an amount of ventilation provided to the patient based on the modified operating parameter associated with the breath rate.

15. The method of claim 13, further comprising:
receiving a physiological parameter associated with the patient from an external device, different than the first or second ventilator;
determining, based on the physiological parameter, that the patient is not receiving a correct amount of ventilation;
modifying, responsive to determining that the patient is not receiving the correct amount of ventilation, an operating parameter associate with a breath rate,
wherein the modified configuration profile is configured to cause the first ventilation device to adjust the amount of ventilation provided to the patient based on the modified operating parameter associated with the breath rate.

16. The method of claim 12, wherein the initial configuration profile is modified for the first ventilation device based on the first ventilation data received from the first ventilation device and the second ventilation data received from the second ventilation device.

17. The method of claim 12, further comprising:
receive the initial configuration profile from the first ventilation device before receiving the first ventilator data from the first ventilation device,
wherein the initial configuration profile received from the first ventilation device is modified based on the received first ventilation data.

18. The method of claim 12, further comprising:
compare the first ventilation data with historical patient data associated with a plurality of patients; and
modify the initial configuration profile based on the comparing of the first ventilation data with the historical patient data associated with a plurality of patients.

19. The method of claim 18, wherein the first ventilation data includes the physiological data obtained from the patient, and wherein the initial configuration profile is modified based on comparing the physiological data with the historical patient data associated with a plurality of patients.

20. A non-transitory machine-readable storage medium comprising machine-readable instructions for causing a processor to execute a method for managing a plurality of ventilators, the method comprising:
storing an initial configuration profile including a set of operating parameters for operating one or more respective ventilation devices;
receiving, over a network, first ventilator data from a first ventilation device at a first location, and second ventilator data from a second ventilation device at a second location, the first and second ventilation devices being configured to operate based on the initial configuration profile, wherein the received first ventilator data comprises one or more current operating parameters of the first ventilation device, or physiological data obtained from a patient associated with the first ventilation device;

modifying the initial configuration profile for use by the first ventilation device based on the received first ventilation data; and providing, over the network, the modified configuration profile to the first ventilation device, wherein the modified configuration profile is configured to be implemented by the first ventilation device after the modified configuration profile is provided to and accepted by the patient associated with the first ventilation device.

* * * * *